(12) United States Patent
Höfgen et al.

(10) Patent No.: US 7,166,637 B2
(45) Date of Patent: Jan. 23, 2007

(54) HYDROXYINDOLES, THEIR USE AS INHIBITORS OF PHOSPHODIESTERASE 4, AND PROCESSES FOR PREPARING THEM

(75) Inventors: Norbert Höfgen, Ottendorf-Okrilla (DE); Hildegard Kuss, Dresden (DE); Ute Egerland, Radebeul (DE); Chris Rundfeldt, Coswig (DE); Helge Hartenhauer, Dresden (DE); Antje Gasparic, Coswig (DE)

(73) Assignee: Elbion AG, Radebeul (DE)

( * ) Notice: Subject to any disclaimer, the term of this patent is extended or adjusted under 35 U.S.C. 154(b) by 321 days.

(21) Appl. No.: 10/714,568

(22) Filed: Nov. 13, 2003

(65) Prior Publication Data
US 2004/0147759 A1    Jul. 29, 2004

(30) Foreign Application Priority Data
Nov. 15, 2002    (DE) ................ 102 53 426

(51) Int. Cl.
*A61K 31/404*    (2006.01)
*C07D 209/04*    (2006.01)

(52) U.S. Cl. ............ 514/419; 548/469; 548/490; 548/491; 546/268.1; 546/276.4; 546/278.1; 514/336; 514/339; 514/415

(58) Field of Classification Search ........ 548/469, 548/492, 491, 490; 546/268.1, 276.4, 277.4, 546/278.1; 514/336, 339, 415, 419
See application file for complete search history.

(56) References Cited

U.S. PATENT DOCUMENTS

| 4,952,587 | A | * | 8/1990 | Baker et al. ........... 514/305 |
| 5,464,861 | A | * | 11/1995 | Dobrusin et al. ........ 514/414 |
| 5,556,874 | A | * | 9/1996 | Dobrusin et al. ........ 514/339 |
| 5,567,711 | A | | 10/1996 | Sheppard et al. |
| 6,008,231 | A | | 12/1999 | Lebaut et al. |
| 6,251,923 | B1 | | 6/2001 | Hofgen et al. |
| 6,545,025 | B1 | | 4/2003 | Hofgen et al. |
| 6,545,158 | B1 | | 4/2003 | Hofgen et al. |
| 6,602,890 | B1 | | 8/2003 | Hofgen et al. |
| 6,613,794 | B1 | | 9/2003 | Hofgen et al. |
| 2002/0111351 | A1 | | 8/2002 | Hofgen et al. |
| 2002/0115651 | A1 | | 8/2002 | Hofgen et al. |
| 2002/0119971 | A1 | | 8/2002 | Hofgen et al. |
| 2002/0137745 | A1 | | 9/2002 | Hofgen et al. |
| 2003/0134876 | A1 | | 7/2003 | Hofgen et al. |

FOREIGN PATENT DOCUMENTS

DE    198 18 964 A1    11/1999
DE    100 53 275 A1    5/2002
WO    WO 2004/000832    12/2003

OTHER PUBLICATIONS

Baker et al (1990): STN International HCAPLUS database, Columbus (Ohio), accession No. 1990:139035.*
Dillard et al (1996): STN International HCAPLUS database, Columbus (Ohio), accession No. 1996:713059.*
Barnes, Chronic obstructive pulmonary disease: new opportunities for drug development, TiPS—Oct. 1998 (vol. 19).
Beavo, et al., Multiple Cyclic Nucleotide Phosphodiesterses, Molecular Pharmacology, 46, 1994.
Bertaccini, et al., Synthesis and pharmacological activity of some 5-methoxyidole derivatives occuring in nature, Il Farmaco, N. 4, Apr. 1967.
Grossman, The value of antibiotics and the outcomes of antibiotic therapy in exacerbations of COPD, CHEST, 113/4, 1998.
Hall, Isoenzyme selective phosphodiesterase inhibitiors: potential clinical uses, J. Clin. Pharmac., 1993, 35.
Jersmann, et al., Enhancement of lipopolysaccharide-induced neutrophil oxygen radical production by tumor necrosis factor alpha, Infection and Immunity, Apr. 1998.
Karlsson, et al., Phosphodiesterase 4 inhibitors for the treatment of asthma, Ashley Publication Ltd., 1997.
Kummer, Asthma und COPD, Atemw.-Lungenkrkh.Jahrgang 20, No. 5, 1994.
Norman, COPD: new developments and therapeutic opportunities, Drugs News Prospect 11(7), Sep. 1998.
Rennard, COPD: overview of definitions, epidemiology, and factors influencing its development, CHEST, 113/4, Apr. 1998.
Schudt, et al., Phosphodiesterase inhibitors, Academic Press, 1996.
Thorphy, et al., Phosphodiesterase inhibitors: new opportunities for the treatment of asthma, Thorax, 1991.
Thorphy, et al., Novel phosphodiesterase inhibitors for the therapy of asthma, DN&P 6(4), May 1993.
Wenisch, et al., Effect of pentoxifylline in vitro on neutrophil reactive oxygen production and phagocytic ability assessed by flow cytometry, Clin. Drug Invest., Feb. 1997.
Wilson, The role of infection in COPD, CHEST, 1998.

* cited by examiner

*Primary Examiner*—Golam M. M. Shameem
(74) *Attorney, Agent, or Firm*—Fulbright & Jaworski L.L.P.

(57) ABSTRACT

The invention relates to substituted 4- or/and 7-hydroxyindoles, to processes for preparing them, to pharmaceutical preparations which comprise these compounds and to the pharmaceutical use of these compounds, which are inhibitors of phosphodiesterase 4, as active compounds for treating diseases which can be influenced by using the compounds according to the invention to inhibit phosphodiesterase 4 activity in immunocompetent cells (e.g. macrophages and lymphocytes).

16 Claims, No Drawings

HYDROXYINDOLES, THEIR USE AS INHIBITORS OF PHOSPHODIESTERASE 4, AND PROCESSES FOR PREPARING THEM

The invention relates to substituted 4- or/and 7-hydroxyindoles, to processes for preparing them, to pharmaceutical preparations which comprise these compounds and to the pharmaceutical use of these compounds, which are inhibitors of phosphodiesterase 4, as active compounds for treating diseases which can be influenced by using the compounds according to the invention to inhibit phosphodiesterase 4 activity in immunocompetent cells (e.g. macrophages and lymphocytes).

Activation of cell membrane receptors by transmitters leads to activation of the second messenger system. Adenylate cyclase synthesizes the active cyclic AMP [cAMP] or cyclic GMP [cGMP] from AMP and GMP, respectively. The cyclic AMP and cyclic GMP give rise, for example, to relaxation in smooth muscle cells or to inhibition of mediator release or synthesis in inflammatory cells. The second messengers cAMP and cGMP are broken down by the phosphodiesterases (PDEs). To date, 11 families of PDE enzymes (PDE1–11) are known, with these families differing from each other in their substrate specificity (cAMP, cGMP or both) and they are dependent on other substrates (e.g. calmodulin). These isoenzymes possess different functions in the body and are expressed to different extents in the individual cell types (Beavo, J A, Conti, M and Heaslip, R J, Multiple cyclic nucleotide phosphodiesterases, Mol. Pharmacol. 1994, 46: 399–405; Hall, I P, Isoenzyme selective phosphodiesterase inhibitors: potential clinical uses, Br. J. clin. Pharmacol. 1993, 35: 1–7). Inhibiting the different PDE isoenzyme types results in cAMP and/or CGMP accumulating in cells, a situation which can be used therapeutically (Torphy, T J, Livi, G P, Christensen, S B, Novel phosphodiesterase Inhibitors for the Therapy of Asthma, Drug News and Perspectives 1993, 6: 203–214).

Type 4 is the predominant PDE isoenzyme in the cells (lymphocytes, mast cells, eosinophilic granulocytes, macrophages) which are of importance for allergic inflammations (Torphy, J T and Undem, B J, phosphodiesterase inhibitors: new opportunities for the treatment of asthma, Thorax 1991, 46: 512–523). Using suitable inhibitors to inhibit PDE 4 is therefore regarded as being an important approach for treating a large number of allergically induced diseases (Schudt, Ch, Dent, G, Rabe, K, Phosphodiesterase Inhibitors, Academic Press London 1996).

The important property of phosphodiesterase 4 inhibitors is their ability to inhibit the release of tumour necrosis factor α (TNFα) from inflammatory cells. TNFα is an important proinflammatory cytokine which exerts an influence on a large number of biological processes. TNFα is released, for example, from activated macrophages, activated T-lymphocytes, mast cells, basophils, fibroblasts, endothelial cells and astrocytes in the brain. It has a self-activating effect on neutrophils, eosinophils, fibroblasts and endothelial cells, resulting in a variety of tissue-destroying mediators being released. In monocytes, macrophages and T lymphocytes, TNFα brings about an increase in the production of other proinflammatory cytokines, such as GM-CSF (granulocyte-macrophage colony-stimulating factor) or interleukin 8. As a result of its inflammation-promoting and catabolic effect, TNFα plays a central role in a large number of diseases, such as inflammations of the airways, inflammations of the joints, endotoxic shock, tissue rejections, AIDS and many other immunological diseases. Inhibitors of phosphodiesterase 4 are consequently also suitable for treating these TNFα-associated diseases. Chronic obstructive pulmonary diseases, COPD, are widespread in the population and are also of great economic importance. Thus, COPD diseases are responsible for approx. 10–15% of all disease costs in the developed countries and approx. 25% of all deaths in the USA can be attributed to this cause (Norman, P.: COPD: New developments and therapeutic opportunities, Drug News Perspect. 11(7), 431–437, 1998), although it is true that the patients are usually aged over 55 at the time of death (Nolte, D: Chronische Bronchitis—eine Volkskrankheit multifaktorieller Genese [Chronic bronchitis—a widespread disease of multifactorial origin], Atemw.-Lungenkrkh. [Airway-lung diseases] 20(5), 260–267, 1994). The WHO estimates that COPD will be the third most frequent cause of death within the next 20 years.

The clinical picture of chronic obstructive pulmonary diseases (COPDs) encompasses a variety of clinical pictures of chronic bronchitides, involving the symptoms of coughing and expectoration, and also progressive and irreversible deterioration in lung function (expiration is particularly affected). The cause of the disease is episodic and frequently complicated by bacterial infections (Rennard, S I: COPD: Overview of definitions, Epidemiology, and factors influencing its development, Chest, 113(4) Suppl., 235S–241S, 1998). During the course of the disease, pulmonary function declines steadily and the lung becomes increasingly emphysematous and the difficulty patients have in breathing becomes evident. This disease markedly impairs the quality of life of patients (shortness of breath, low exercise tolerance) and significantly reduces their life expectancy. Apart from environmental factors, the main risk factor is smoking (Kummer, F: Asthma und COPD [Asthma and COPD.] Atemw.-Lungenkrkh. [Airway-lung diseases] 20(5), 299–302, 1994; Rennard, S I: COPD: overview of definitions, Epidemiology, and factors influencing its development, Chest, 113(4) Suppl., 235S–241S, 1998) and men are therefore much more frequently affected than are women. However, this picture will shift in the future as a result of changes in custom and the increase in the number of female smokers.

Current therapy is only aimed at alleviating the symptoms without attacking the causes for the progression in the disease. The use of long-acting beta2 agonists (e.g. salmeterol), where appropriate in combination with muscarinergic antagonists (e.g. ipratropium), improves lung function as a result of bronchodilatation and is employed routinely (Norman, P: COPD: New developments and therapeutic opportunities, Drug News Perspect. 11(7), 431–437, 1998). Bacterial infections, which have to be treated with antibiotics, play an important role in the COPD episodes (Wilson, R: The role of infection in COPD, Chest, 113(4) Suppl. 242S–248S, 1998; Grossman, R F: The value of antibiotics and the outcomes of antibiotic therapy in exacerbations of COPD, Chest, 113(4) Suppl., 249S–255S, 1998). The therapy of this disease is still unsatisfactory, particularly in view of the steady decline in lung function. Novel therapeutic approaches which are directed against inflammation mediators, proteases or adhesion molecules could be very promising (Barnes, P J: Chronic obstructive disease: new opportunities for drug development, TiPS 10(19), 415–423, 1998).

Independently of the bacterial infections which complicate the disease, a chronic inflammation, which is dominated by neutrophilic granulocytes, can be found in the bronchi. The mediators and enzymes which are released by neutrophilic granulocytes are thought to be responsible, inter alia, for the structural changes which are observed in the airways (emphysema). Consequently, inhibiting the activity of the neutrophilic granulocytes is a rational approach for preventing or retarding the progress of the COPD (deterioration in lung function parameters). The proinflammatory cytokine TNFα (tumour necrosis factor) is an important stimulus for activating the granulocytes. Thus, it is known that TNFα stimulates the formation of oxygen radicals by neutrophilic granulocytes (Jersmann, H P A; Rathjen, D A and Ferrante, A: Enhancement of LPS-induced neutrophil oxygen radical production by TNFα, Infection and Immunity, 4, 1744–1747, 1998). PDE 4 inhibitors are able very effectively to inhibit the release of TNFα from a large number of cells and consequently suppress the activity of the neutrophilic granulocytes. The non-specific PDE inhibitor pentoxifylline is able to inhibit both the formation of oxygen radicals and the ability of neutrophilic granulocytes to phagocytose (Wenisch, C; Zedwitz-Liebenstein, K; Parschalk, B and Graninger, W: Effect of pentoxifylline in vitro on neutrophil reactive oxygen production and phagocytic ability assessed by flow cytometry, Clin. Drug Invest., 13(2): 99–104, 1997).

A variety of PDE 4 inhibitors are already known. These are primarily xanthine derivatives, rolipram analogues or nitraquazone derivatives (review in: Karlsson, J-A, Aldos, D, Phosphodiesterase 4 inhibitors for the treatment of asthma, Exp. Opin. Ther. Patents 1997, 7: 989–1003). It has not thus far been possible to bring any of these compounds into clinical use. It has come to be realized that the known PDE 4 inhibitors also possess a variety of side-effects, such as nausea and vomiting, which it has not thus far been possible to suppress adequately. It is therefore necessary to discover new PDE 4 inhibitors which have better therapeutic breadth.

Indol-3-ylglyoxylamides, and methods for preparing them, have already been described on a number of occasions. In every case, indoles which are unsubstituted in the 3 position, and which were synthesized by substituting a commercially available indole in the 1 position, were converted, by reaction with oxalyl halides, into indol-3-ylgly-oxylyl halides, which then, by reacting with ammonia or with primary or secondary amines, give the corresponding indol-3-ylglyoxylamides (Scheme 1).

Scheme 1

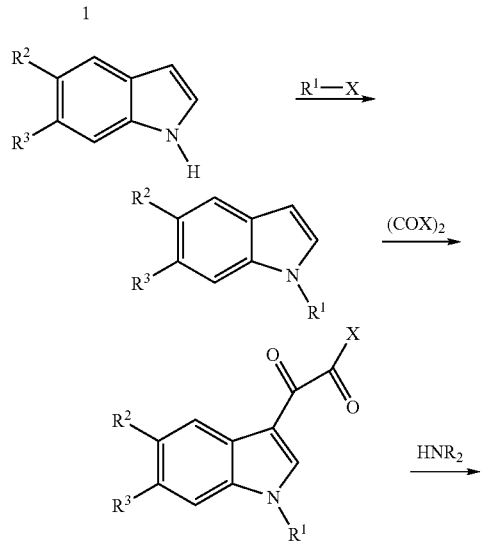

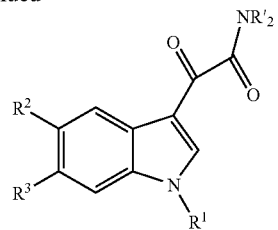

X = halogen

Thus, the patents U.S. Pat. No. 2,825,734 and U.S. Pat. No. 3,188,313 describe various indol-3-ylglyoxylamides which are prepared in accordance with Scheme 1. These compounds were used as intermediates for preparing indole derivatives which were formed by reductions. The patent U.S. Pat. No. 3,642,803 also describes indol-3-ylglyoxylamides.

Farmaco 22 (1967), 229–244 describes the preparation of 5-methoxyindol-3-ylglyoxylamides. Once again, the indole derivative which is employed is reacted with oxalyl chloride and the resulting indol-3-ylglyoxylyl chloride is reacted with an amine.

In addition, the patent U.S. Pat. No. 6,008,231 also describes indol-3-ylglyoxylamides and methods for preparing them. Once again, use is made of the reaction steps and reaction conditions depicted in Scheme 1. 4- or 7-hydroxyindole derivatives are not described.

Substituted 5-hydroxyindolylglyoxylamides and 6-hydroxyindolylglyoxylamides, and methods for preparing them, and their use as PDE 4 inhibitors, were described for the first time in patent application DE 198 18 964 A1. However, 4- or 7-hydroxyindole derivatives, and their preparation and use, are not disclosed.

The invention relates to substituted hydroxyindoles of the general formula 1,

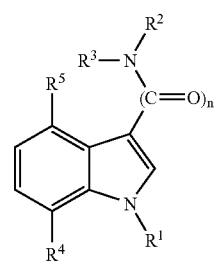

in which
n can be=1 or 2, and
$R^1$
(i) is —$C_{1-10}$-alkyl, which is straight-chain or branched and optionally substituted, once or more than once, by —OH, —SH, —$NH_2$, —$NHC_{1-6}$-alkyl, —$N(C_{1-6}$-alkyl$)_2$, —$NHC_{6-14}$aryl, —$N(C_{6-14}$aryl$)_2$, —$N(C_{16}$alkyl) ($C_{6-14}$ aryl), —$NO_2$, —CN, —F, —Cl, —Br, —I, —O—$C_{1-6}$-alkyl, —O—$C_{6-14}$-aryl, —S—$C_{1-6}$-alkyl, —S—$C_{6-14}$ aryl, —$SO_3H$, —$SO_2C_{1-6}$alkyl, —$SO_2C_{6-14}$aryl, —$OSO_2C_{1-6}$alkyl, —$OSO_2C_{6-14}$aryl, —COOH, —(CO) $C_{15}$alkyl or —O(CO)$C_{1-5}$alkyl, by mono-, bi- or tricyclic saturated or monounsaturated or polyunsaturated carbocycles having 3–14 ring members, or by mono-, bi- or tricyclic saturated or monounsaturated or polyunsaturated heterocycles having 5–15 ring members and 1–6 heteroatoms which are preferably N, O and S, where the $C_{6-14}$aryl groups and the carbocyclic and heterocyclic substituents can, for their part, be optionally substituted, once or more than once, by —$C_{1-6}$-alkyl, —OH, —$NH_2$, —$NHC_{1-6}$-alkyl, —$N(C_{1-6}$-alkyl$)_2$, —$NO_2$, —CN, —F, —Cl, —Br, —I, —O—$C_{1-6}$-alkyl, —S—$C_{1-6}$-alkyl, —$SO_3H$, —$SO_2C_{1-6}$alkyl, —$OSO_2C_{1-6}$alkyl, —COOH, —(CO)$C_{1-5}$alkyl or —O(CO)$C_{1-5}$alkyl, and where the alkyl groups on the carbocyclic and heterocyclic substituents can, for their part, be optionally substituted, once or more than once, by —OH, —SH, —$NH_2$, —F, —Cl, —Br, —I, —$SO_3H$ or —COOH, or (ii) is —$C_{2-10}$-alkenyl, which is monounsaturated or polyunsaturated, straight-chain or branched and optionally substituted, once or more than once, by —OH, —SH, —$NH_2$, —$NHC_{1-6}$-alkyl, —$N(C_{1-6}$-alkyl$)_2$, —$NHC_{6-14}$aryl, —$N(C_{6-14}$aryl$)_2$, —$N(C_{1-6}$alkyl)($C_{6-14}$aryl), —$NO_2$, —CN, —F, —Cl, —Br, —I, —O—$C_{1-6}$-alkyl, —O—$C_{6-14}$-aryl, —S—$C_{1-6}$-alkyl, —S—$C_{6-14}$aryl, —$SO_3H$, —$SO_2C_{1-6}$alkyl, —$SO_2C_{6-14}$aryl, —$OSO_2C_{1-6}$alkyl, —$OSO_2C_{6-14}$-aryl, —COOH, —(CO)$C_{1-5}$-alkyl or —O(CO)$C_{1-5}$alkyl, by mono-, bi- or tricyclic saturated or monounsaturated or polyunsaturated carbocycles having 3–14 ring members, or by mono-, bi- or tricyclic saturated or monounsaturated or polyunsaturated heterocycles having 5–15 ring members and 1–6 heteroatoms which are preferably N, O and S, where the $C_{6-14}$aryl groups and the carbocyclic and heterocyclic substituents can, for their part, be optionally substituted, once or more than once, by —$C_{1-6}$-alkyl, —OH, —$NH_2$, —$NHC_{1-6}$-alkyl, —$N(C_{1-6}$-alkyl$)_2$, —$NO_2$, —CN, —F, —Cl, —Br, —I, —O—$C_{1-6}$-alkyl, —S—$C_{1-6}$-alkyl, —$SO_3H$, —$SO_2C_{1-6}$alkyl, —$OSO_2C_{1-6}$alkyl, —COOH, —(CO)$C_{1-5}$alkyl or —O(CO)$C_{1-5}$alkyl, and where the alkyl groups on the carbocyclic and heterocyclic substituents can, for their part, be optionally substituted, once or more than once, by —OH, —SH, —$NH_2$, —F, —Cl, —Br, —I, —$SO_3H$ or —COOH, $R^2$ and $R^3$ (i) are, in each case independently of each other, hydrogen or —$C_{1-5}$-alkyl, which is optionally substituted, once or more than once, by —OH, —SH, —$NH_2$, —$NHC_{1-6}$-alkyl, —$N(C_{1-6}$-alkyl$)_2$, —$NO_2$, —CN, —F, —Cl, —Br, —I, —O—$C_{1-6}$-alkyl, —S—$C_{1-6}$-alkyl, -phenyl or -pyridyl, -phenyl, which is optionally substituted, once or more than once, by —$C_{1-3}$-alkyl, —OH, —SH, —$NH_2$, —$NHC_{1-3}$-alkyl, —$N(C_{1-3}$-alkyl$)_2$, —$NO_2$, —CN, —COOH, —$COOC_{1-3}$-alkyl, —F, —Cl, —Br, —I, —O—$C_{1-3}$-alkyl, —S—$C_{1-3}$-alkyl or —O(CO)—$C_{1-3}$-alkyl, -pyridyl, which is optionally substituted, once or more than once, by —$C_{1-3}$-alkyl, —OH, —SH, —$NO_2$, —CN, —COOH, —$COOC_{1-3}$-alkyl, —F, —Cl, —Br, —I, —O—$C_{1-3}$-alkyl, —S—$C_{1-3}$-alkyl or —O(CO)—$C_{1-3}$-alkyl, where only one of $R^2$ and $R^3$ is hydrogen and where the alkyl groups on the carbocyclic and heterocyclic substituents can, for their part, be optionally substituted, once or more than once, by —OH, —SH, —$NH_2$, —F, —Cl, —Br, —I, —$SO_3H$, —COOH, —(CO)—$C_{1-5}$-alkyl, or —O(CO)$C_{1-5}$-alkyl, or (ii) $NR^2R^3$ together form a saturated or unsaturated five-membered or six-membered ring which can contain up to 3 heteroatoms, preferably N, S and O, and which is optionally substituted, once or more than once, by —$C_{1-3}$-alkyl, —OH, —SH, —$NO_2$, —CN, —COOH, —$COOC_{1-3}$-alkyl, —F, —Cl, —Br, —I, —O—$C_{1-3}$-alkyl, —S—$C_{1-3}$-alkyl or —O(CO)—$C_{1-3}$-alkyl, $R^4$ and $R^5$ are —H or —OH, where at least one of the two must be —OH.

In the compounds 1, n preferably has the meaning 2. Furthermore, $R^4$ preferably has the meaning —OH and $R^5$ the meaning H. $NR^2R^3$ is preferably a phenyl amino group or pyridyl amino group which is substituted by one or more halogen atoms, e.g. F, Cl, Br or I. $R^1$ is advantageously a substituted benzyl radical, with a substituent on the phenyl ring preferably being in the ortho position to the benzyl methylene group. In addition, the compounds mentioned in the experimental examples are also particularly preferred.

The invention furthermore relates to the physiologically tolerated salts of the compounds according to formula 1.

The physiologically tolerated salts are obtained in a customary manner by neutralizing the bases with inorganic or organic acids or by neutralizing the acids with inorganic or organic bases. Examples of suitable inorganic acids are hydrochloric acid, sulphuric acid, phosphoric acid or hydrobromic acid, while examples of suitable organic acids are carboxylic acid, sulpho acid or sulphonic acid, such as acetic acid, tartaric acid, lactic acid, propionic acid, glycolic acid, malonic acid, maleic acid, fumaric acid, tannic acid, succinic acid, alginic acid, benzoic acid, 2-phenoxybenzoic acid, 2-acetoxybenzoic acid, cinnamic acid, mandelic acid, citric acid, maleic acid, salicylic acid, 3-aminosalicylic acid, ascorbic acid, embonic acid, nicotinic acid, isonicotinic acid, oxalic acid, amino acids, methanesulphonic acid, ethanesulphonic acid, 2-hydroxyethanesulphonic acid, ethane-1,2-disulphonic acid, benzenesulphonic acid, 4-methylbenzenesulphonic acid or naphthalene-2-sulphonic acid. Examples of suitable inorganic bases are sodium hydroxide, potassium hydroxide and ammonia, while examples of suitable organic bases are amines, preferably, however, tertiary amines, such as trimethylamine, triethylamine, pyridine, N,N-dimethylaniline, quinoline, isoquinoline, α-picoline, β-picoline, γ-picoline, quinaldine and pyrimidine.

In addition, physiologically tolerated salts of the compounds according to formula 1 can be obtained by converting derivatives which possess tertiary amino groups into the corresponding quaternary ammonium salts in a manner known per se using quaternizing agents. Examples of suitable quaternizing agents are alkyl halides, such as methyl iodide, ethyl bromide and n-propyl chloride, and also arylalkyl halides, such as benzyl chloride or 2-phenylethyl bromide.

Furthermore, in the case of the compounds of the formula 1 which contain an asymmetric carbon atom, the invention relates to the D form, the L form and D,L mixtures and also, where more than one asymmetric carbon atom is present, to the diastereomeric forms. Those compounds of the formula 1 which contain asymmetric carbon atoms, and which as a rule accrue as racemates, can be separated into the optically active isomers in a known manner, for example using an optically active acid. However, it is also possible to use an optically active starting substance from the outset, with a corresponding optically active or diastereomeric compound then being obtained as the end product.

The compounds according to the invention have been found to have pharmacologically important properties which can be used therapeutically. The compounds according to formula 1 can be used on their own, in combination with each other or in combination with other active compounds.

The compounds according to the invention are inhibitors of phosphodiesterase 4. It is therefore a part of the subject-matter of this invention that the compounds according to formula 1, and their salts and also pharmaceutical preparations which comprise these compounds or their salts, can be used for treating diseases in which inhibiting phosphodiesterase 4 is of value.

These diseases include, for example joint inflammations, including arthritis and rheumatoid arthritis and also other arthritic diseases, such as rheumatoid spondylitis and osteoarthritis. Other possible applications are the treatment of patients who are suffering from osteoporosis, sepsis, septic shock, Gram-negative sepsis, toxic shock syndrome, dyspnoea syndrome, asthma or other chronic pulmonary diseases, such as COPD, bone resorption diseases or transplant rejection reactions, or other autoimmune diseases, such as lupus erythematosus, multiple sclerosis, glomerulonephritis and uveitis, insulin-dependent diabetes mellitus and chronic demyelination.

In addition, the compounds according to the invention can also be used for treating infections, such as viral infections and parasite infections, for example for treating malaria, leishmaniasis, infection-induced fever, infection-induced muscular pains, AIDS and cachexias, and also nonallergic rhinitis.

The compounds according to the invention can also be used as bronchodilators and for asthma prophylaxis.

Furthermore, the compounds according to formula 1 are inhibitors of the accumulation and activity of eosinophils. As a consequence, the compounds according to the invention can also be used in connection with diseases in which eosinophils play a role. These diseases include, for example, inflammatory airway diseases, such as bronchial asthma, allergic rhinitis, allergic conjunctivitis, atopic dermatitis, eczemas, allergic angiitis, eosinophil-induced inflammations, such as eosinophilic fasciitis, eosinophilic pneumonia and PIE (pulmonary Infiltration involving eosinophilia) syndrome, urticaria, ulcerative colitis, Crohn's disease and proliferative skin diseases, such as psoriasis or keratosis.

It is also part of the subject-matter of this invention that the compounds according to formula 1 and their salts are also able to inhibit LPS-induced pulmonary neutrophil infiltration in rats in vivo. The pharmacologically important properties which have been found verify that the compounds according to formula 1, and their salts and also pharmaceutical preparations which comprise these compounds or their salts, can be used therapeutically for treating chronic obstructive lung diseases.

The compounds according to the invention furthermore possess neuroprotective properties and can be used for treating diseases in which neuroprotection is of value. Examples of these diseases are senile dementia (Alzheimer's disease), loss of memory, Parkinson's disease, depressions, strokes and intermittent claudication.

Other possible applications of the compounds according to the invention are the prophylaxes and therapy of prostate diseases, such as benign prostate hyperplasia, pollakiuria, nocturia and the treatment of incontinence, of colic caused by urinary calculi, and of male and female sexual dysfunctions.

Finally, the compounds according to the invention can also be used for inhibiting the development of pharmaceutical dependency in connection with the repeated use of analgesics, such as morphine, and for using the development of tolerance in connection with the repeated use of the analgesics.

An effective dose of the compounds according to the invention, or their salts, is used, in addition to the customary auxiliary substances, carrier substances and additives, for producing the pharmaceuticals. The dose of the active compounds can vary depending on the route of administration, the age and weight of the patient, the nature and severity of the diseases to be treated, and similar factors. The daily dose can be given as a single dose, which is to be administered once, or be subdivided into two or more daily doses, and is as a rule 0.001–100 mg. Particular preference is given to administering daily doses of 0.1–50 mg.

Suitable administration forms are oral, parenteral, intravenous, transdermal, topical, inhalative and intranasal preparations. Particular preference is given to using topical, inhalative and intranasal preparations of the compounds according to the invention. The customary galenic preparation forms, such as tablets, sugar-coated tablets, capsules, dispersible powders, granulates, aqueous solutions, aqueous or oily suspensions, syrups, juices or drops, are used.

Solid medicinal forms can comprise inert components and carrier substances, such as calcium carbonate, calcium phosphate, sodium phosphate, lactose, starch, mannitol, alginates, gelatine, guar gum, magnesium stearate, aluminium stearate, methyl cellulose, talc, highly dispersed silicic acids, silicone oil, higher molecular weight fatty acids, (such as stearic acid), gelatine, agar agar or vegetable or animal fats and oils, or solid high molecular weight polymers (such as polyethylene glycol); preparations which are suitable for oral administration can comprise additional flavourings and/or sweetening agents, if desired.

Liquid medicinal forms can be sterilized and/or, where appropriate, comprise auxiliary substances, such as preservatives, stabilizers, wetting agents, penetrating agents, emulsifiers, spreading agents, solubilizers, salts, sugars or sugar alcohols for regulating the osmotic pressure or for buffering, and/or viscosity regulators.

Examples of such additives are tartrate and citrate buffers, ethanol and sequestering agents (such as ethylenediaminetetraacetic acid and its non-toxic salts). High molecular weight polymers, such as liquid polyethylene oxides, microcrystalline celluloses, carboxymethyl celluloses, polyvinylpyrrolidones, dextrans or gelatine, are suitable for regulating the viscosity. Examples of solid carrier substances are starch, lactose, mannitol, methyl cellulose, talc, highly dispersed silicic acids, high molecular weight fatty acids (such as stearic acid), gelatine, agar agar, calcium phosphate, magnesium stearate, animal and vegetable fats, and solid high molecular weight polymers, such as polyethylene glycol.

Oily suspensions for parenteral or topical applications can be vegetable synthetic or semisynthetic oils, such as liquid fatty acid esters having in each case from 8 to 22 C atoms in the fatty acid chains, for example palmitic acid, lauric acid, tridecanoic acid, margaric acid, stearic acid, arachidic acid, myristic acid, behenic acid, pentadecanoic acid, linoleic acid, elaidic acid, brasidic acid, erucic acid or oleic acid, which are esterified with monohydric to trihydric alcohols having from 1 to 6 C atoms, such as methanol, ethanol, propanol, butanol, pentanol or their isomers, glycol or glycerol. Examples of such fatty acid esters are commercially available miglyols, isopropyl myristate, isopropyl palmitate, isopropyl stearate, PEG 6-capric acid, caprylic/capric acid esters of saturated fatty alcohols, polyoxyethylene glycerol trioleates, ethyl oleate, waxy fatty acid esters, such as artificial ducktail gland fat, coconut fatty acid isopropyl ester, oleyl oleate, decyl oleate, ethyl lactate, dibutyl phthalate, diisopropyl adipate, polyol fatty acid esters, inter alia. Silicone oils of differing viscosity, or fatty alcohols, such as isotridecyl alcohol, 2-octyldodecanol, cetylstearyl alcohol or oleyl alcohol, or fatty acids, such as oleic acid, are also suitable. It is furthermore possible to use vegetable oils, such as castor oil, almond oil, olive oil, sesame oil, cotton seed oil, groundnut oil or soybean oil.

Suitable solvents, gelatinizing agents and solubilizers are water or water-miscible solvents. Examples of suitable substances are alcohols, such as ethanol or isopropyl alcohol, benzyl alcohol, 2-octyldodecanol, polyethylene glycols, phthalates, adipates, propylene glycol, glycerol, di- or tripropylene glycol, waxes, methyl cellosolve, cellosolve, esters, morpholines, dioxane, dimethyl sulphoxide, dimethylformamide, tetrahydrofuran, cyclohexanone, etc.

Cellulose ethers which can dissolve or swell both in water or in organic solvents, such as hydroxypropylmethyl cellulose, methyl cellulose or ethyl cellulose, or soluble starches, can be used as film-forming agents.

Mixtures of gelatinizing agents and film-forming agents are also perfectly possible. In this case, use is made, in particular, of ionic macromolecules such as sodium carboxymethyl cellulose, polyacrylic acid, polymethacrylic acid and their salts, sodium amylopectin semiglycolate, alginic acid or propylene glycol alginate as the sodium salt, gum arabic, xanthan gum, guar gum or carrageenan. The following can be used as additional formulation aids: glycerol, paraffin of differing viscosity, triethanolamine, collagen, allantoin and novantisolic acid. Use of surfactants, emulsifiers or wetting agents, for example of Na lauryl sulphate, fatty alcohol ether sulphates, di-Na-N-lauryl-β-iminodipropionate, polyethoxylated castor oil or sorbitan monooleate, sorbitan monostearate, polysorbates (e.g. Tween), cetyl alcohol, lecithin, glycerol monostearate, polyoxyethylene stearate, alkylphenol polyglycol ethers, cetyltrimethylammonium chloride or mono-/dialkylpolyglycol ether orthophosphoric acid monoethanolamine salts can also be required for the formulation. Stabilizers, such as montmorillonites or colloidal silicic acids, for stabilizing emulsions or preventing the breakdown of active substances such as antioxidants, for example tocopherols or butylhydroxyanisole, or preservatives, such as p-hydroxybenzoic acid esters, can likewise be used for preparing the desired formulations.

Preparations for parenteral administration can be present in separate dose unit forms, such as ampoules or vials. Use is preferably made of solutions of the active compound, preferably aqueous solution and, in particular, isotonic solutions and also suspensions. These injection forms can be made available as ready-to-use preparations or only be prepared directly before use, by mixing the active compound, for example the lyophilisate, where appropriate containing other solid carrier substances, with the desired solvent or suspending agent.

Intranasal preparations can be present as aqueous or oily solutions or as aqueous or oily suspensions. They can also be present as lyophilisates which are prepared before use using the suitable solvent or suspending agent.

The preparations are produced, aliquoted and sealed under the customary antimicrobial and aseptic conditions.

The invention furthermore relates to processes for preparing the compounds according to the invention.

According to the invention, the compounds of the general formula 1, having the previously described meanings of $R^1$, $R^2$, $R^3$, $R^4$, $R^5$ and n=1,

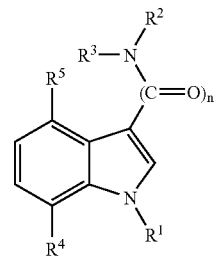

are prepared by initially converting indole-3-carboxylic acids of the formula 2 having an identical meaning of $R^1$,

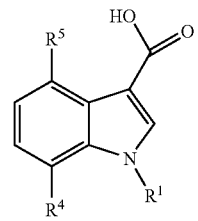

in which $R^4$ and $R^5$ are —H or —$OR^6$, where at least one of the two must be —$OR^6$ and $R^6$ is a protecting group or leaving group, in particular alkyl, cycloalkyl, arylalkyl, aryl, heteroaryl, acyl, alkoxycarbonyl, aryloxycarbonyl, aminocarbonyl, N-substituted aminocarbonyl, silyl or sulphonyl groups, and also sequestering agents, such as compounds of boric acid or of phosphoric acid, and also covalently or coordinately bound metals, such as zinc, aluminium or copper, in a manner known per se, using acid chlorides, preferably using thionyl chloride or oxalyl chloride, into the analogous indole-3-carbonyl chlorides of the formula 3.

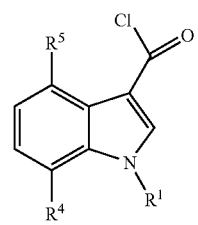

Compounds of the general formula 1, having the previously described meanings of $R^1$, $R^2$ and $R^3$ and n=1, and also the meanings for $R^4$ and $R^5$ as described for formulae 2 and 3, are then formed from the isolated indole-3-carbonyl chlorides of the formula 3 by reacting them with a primary or secondary amine. The reaction proceeds advantageously in the presence of an auxiliary base. Auxiliary bases which can be used are an excess of the amine employed as the coreactant, a tertiary amine, preferably pyridine or triethylamine, and inorganic bases, preferably alkali metal hydroxides or alkali metal hydrides.

The compounds of the formula 1 according to the invention are liberated by eliminating the leaving group $R^6$ which is still present in $R^4$ and/or $R^5$.

Both acids and bases, such as hydrobromic acid, hydrochloric acid or hydriodic acid, or sodium hydroxide, potassium hydroxide and sodium carbonate or potassium carbonate, and also activating Lewis acids, such as $AlCl_3$, $BF_3$, $BBr_3$ or LiCl, are employed for eliminating the —$R^6$ substituent. The elimination reaction in each case takes place in the absence or presence of additional activators, such as ethane-1,2-dithiol or benzylmercaptan and also ether cleavages, using hydrogen, under elevated pressure or under normal pressure, in the presence of a suitable catalyst, such as palladium or iridium catalysts.

According to the invention, the compounds of the general formula 1, having the previously described meanings of $R^1$, $R^2$ and $R^3$, and n=2,

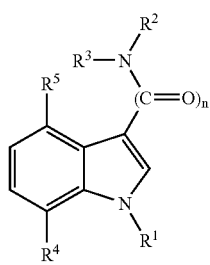

1 are prepared by initially converting indoles of the formula 4, having an identical meaning of $R^1$,

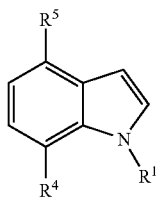

4 in which $R^4$ and $R^5$ are —H or —$OR^6$, where at least one of the two must be —$OR^6$ and $R^6$ is a protecting group or leaving group, in particular alkyl, cycloalkyl, arylalkyl, aryl, heteroaryl, acyl, alkoxycarbonyl, aryloxycarbonyl, aminocarbonyl, N-substituted aminocarbonyl, silyl or sulphonyl groups, and also sequestering agents, such as compounds of boric acid or of phosphoric acid, and also covalently or coordinatively bound metals, such as zinc, aluminium or copper, in a manner known per se, by acylating them with oxalyl chloride, into the analogous indol-3-ylglyoxyl chlorides of the formula 5.

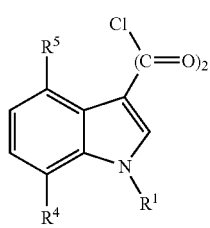

5

Compounds of the general formula 1, having the previously described meanings of $R^1$, $R^2$ and $R^3$, and n=2, and also the meanings for $R^4$ and $R^5$ as described for formulae 4 and 5, are then formed from the isolated indol-3-ylglyoxyl chlorides of the formula 5 by reacting them with a primary or secondary amine. The reaction proceeds advantageously in the presence of an auxiliary base.

Auxiliary bases which can be used are an excess of the amine employed as the coreactant, a tertiary amine, preferably pyridine or triethylamine, and also inorganic bases, preferably alkali metal hydroxides or alkali metal hydrides.

The compounds of the formula 1 according to the invention are liberated by eliminating the leaving group $R^6$ which is still present in $R^4$ and/or $R^5$.

Both acids and bases, such as hydrobromic acid, hydrochloric acid or hydriodic acid, or sodium hydroxide, potassium hydroxide and sodium carbonate or potassium carbonate, and also activating Lewis acids, such as $AlCl_3$, $BF_3$, $BBr_3$ or LiCl, are employed for eliminating the —$R^6$ substituent. The elimination reaction in each case takes place in the absence or presence of additional activators, such as ethane-1,2-dithiol or benzylmercaptan and also ether cleavages, using hydrogen, under elevated pressure or under normal pressure, in the presence of a suitable catalyst, such as palladium or iridium catalysts.

EXAMPLES

Example 1

Preparing N-(3,5-dichloropyrdin-4-yl)-[1-(4-fluorobenzyl)-4-hydroxyindol-3-yl]carboxamide This is an example of a process for preparing compounds of the formula 1 according to the invention in which n=1.

3.22 g of 4-benzyloxy-1-(4-fluorobenzyl)indole-3-carboxylic acid (8.6 mmol) are suspended in 15 ml of dichloromethane. While cooling with water, 1.8 ml of oxalyl chloride (17.4 mmol) are added. The reaction mixture is stirred for 8 hours. During this time, 4-benzyloxy-1-(4-fluorobenzyl)indole-3-carbonyl chloride crystallized out. It is isolated and dissolved in 18 ml of tetrahydrofuran (THF).

1.14 g of sodium hydride (60% strength) are suspended in 21 ml of THF. While the suspension is being stirred at approx. 10° C., a solution of 1.5 g of 4-amino-3,5-dichloropyridine (8.6 mmol) in 21 ml of THF is added dropwise. After approx. 15 minutes, the previously prepared solution of the 4-benzyloxy-1-(4-fluorobenzyl)indole-3-carbonyl chloride is added dropwise to the reaction mixture. After that, the whole is boiled at reflux for 3 hours. 36 ml of ethyl acetate and 36 ml of water are then added to the reaction mixture after it has cooled down. The phases are separated and the organic phase is washed with water. The solvent is distilled off and the residue is recrystallized from ethanol and dried.

The N-(3,5-dichloropyridin-4-yl)-[4-benzyloxy-1-(4-fluorobenzyl)indol-3-yl]carboxamide which has been obtained in this way is dissolved in 100 ml of dichloromethane. The solution is heated to reflux and a solution of 1 ml of $BBr_3$ in 10 ml of dichloromethane is then added dropwise. After that, the mixture is heated to reflux, and while stirring, for a further 3 hours. After it has been cooled down to 10° C., 100 ml of a 1 M solution of $NaHCO_3$ are added, thereby achieving a pH of 8–9. During this procedure, the temperature has to be kept below 20° C. The mixture is subsequently stirred for a further 3 hours. The product, which has crystallized out, is filtered off with suction, washed with water and dried.

The crude product is recrystallized from ethanol.

Yield: 1.4 g (37.8% of theory)

Melting point: 263–265° C.

Example 2

Preparing N-(3,5-dichloropyrdin-4-yl)-[1-(4-chlorobenzyl)-7-hydroxyindol-3-yl]glyoxylamide This is an example of a process for preparing compounds of the formula 1 according to the invention in which n=2:

5.9 g of 7-benzyloxy-1-(4-chlorobenzyl)indole (17 mmol) are dissolved in 50 ml of tert-butyl methyl ether. A solution of 2.6 ml of oxalyl chloride (30 mmol) in 10 ml of tert-butyl methyl ether is added dropwise at 0° C. and while stirring. After that, the mixture is boiled at reflux for 2 hours. The solvent is then distilled off in vacuo. The resulting 7-benzyloxy-1-(4-chlorobenzyl)indole-3-ylglyoxyl chloride is obtained as a solid residue, which is suspended in 50 ml of tetrahydrofuran (THF).

A solution of 2.77 g of 4-amino-3,5-dichloropyridine (17 mmol) in 20 ml of THF is added dropwise, at −5° C., to a suspension of 2.7 g of sodium hydride in 80 ml of THF. After that, the mixture, while being stirred, is kept at a constant temperature of 20° C. for 1 hour. The previously prepared suspension of the 7-benzyloxy-1-(4-chlorobenzyl)indol-3-ylglyoxyl chloride is then added dropwise at approx. 0° C. Finally, the reaction mixture is boiled at reflux for 4 hours. The solvent is removed in vacuo. The residue is stirred up with 50 ml of ethyl acetate and 50 ml of water. The phases are separated. The organic phase is washed with water. The solvent is distilled in vacuo. The residue is recrystallized from isopropanol.

The N-(3,5-dichloropyridin-4-yl)-[7-benzyloxy-1-(4-chlorobenzyl)indol-3-yl]glyoxylamide which has been obtained in this way is dissolved in 100 ml of dichloromethane. The solution is heated to reflux and a solution of 1 ml of $BBr_3$ in 10 ml of dichloromethane is added dropwise. After that, the mixture is heated to reflux, while being stirred, for a further 3 hours. After the mixture has been cooled down to 10° C., 100 ml of a 1 M solution of $NaHCO_3$ are added, thereby achieving a pH of 8–9. During this procedure, the temperature has to be kept below 20° C. The mixture is subsequently stirred for a further 3 hours. The product, which has crystallized out, is filtered off with suction, washed with water and dried. The crude product is recrystallized from ethanol.

Yield: 3.8 g (47.5% of theory)

Melting point: 245–247° C.

Example 3

Preparing Other Compounds

The given preparation process can be used to prepare a large number of other compounds of the formula 1, of which the following are cited by way of example:

| Compound | —$R^1$ | —$NR^2R^3$ | —$R^4$ | —$R^5$ | n |
|---|---|---|---|---|---|
| 1 | 4-fluorobenzyl- | 3,5-dichloro-4-pyridyl-amino- | —H | —OH | 1 |
| 2 | 4-chlorobenzyl- | 3,5-dichloro-4-pyridyl-amino- | —OH | —H | 2 |
| 3 | 4-chlorobenzyl- | 3,5-dichloro-4-pyridyl-amino- | —OH | —H | 1 |
| 4 | 4-fluorobenzyl- | 3,5-dichloro-4-pyridyl-amino- | —H | —OH | 2 |
| 5 | 4-fluorobenzyl- | 3,5-dichloro-4-pyridyl-amino- | —OH | —H | 2 |
| 6 | 2-fluorobenzyl- | 3,5-dichloro-4-pyridyl-amino- | —OH | —H | 2 |
| 7 | 3-nitrobenzyl- | 3,5-dichloro-4-pyridyl-amino- | —OH | —H | 2 |
| 8 | 2,6-difluoro-benzyl- | 3,5-dichloro-4-pyridyl-amino- | —OH | —H | 2 |
| 9 | 2,4-difluoro-benzyl- | 3,5-dichloro-4-pyridyl-amino- | —OH | —H | 2 |
| 10 | 2-chlorobenzyl- | 3,5-dichloro-4-pyridyl-amino- | —OH | —H | 2 |
| 11 | 2,6-dichloro-benzyl- | 3,5-dichloro-4-pyridyl-amino- | —OH | —H | 2 |
| 12 | 2-methyl-benzyl- | 3,5-dichloro-4-pyridyl-amino- | —OH | —H | 2 |
| 13 | 2,6-dimethyl-benzyl- | 3,5-dichloro-4-pyridyl-amino- | —OH | —H | 2 |
| 14 | n-hexyl- | 3,5-dichloro-4-pyridyl-amino- | —OH | —H | 2 |
| 15 | isobutyl- | 3,5-dichloro-4-pyridyl-amino- | —OH | —H | 2 |
| 16 | cyclopropyl-methyl- | 3,5-dichloro-4-pyridyl-amino- | —OH | —H | 2 |
| 17 | 4-fluorobenzyl- | 2,6-dichloro-phenylamino- | —OH | —H | 2 |
| 18 | 2-fluorobenzyl- | 2,6-dichloro-phenylamino- | —OH | —H | 2 |
| 19 | 2-fluorobenzyl- | 4-pyridylamino- | —OH | —H | 2 |
| 20 | 4-pyridyl-methyl- | 3,5-dichloro-4-pyridyl-amino- | —OH | —H | 2 |
| 21 | 4-fluorobenzyl- | Piperidyl- | —OH | —H | 2 |
| 22 | 4-hydroxy-benzyl- | 3,5-dichloro-4-pyridyl-amino- | —OH | —H | 2 |
| 23 | 2-chloro-6-fluoro-benzyl- | 3,5-dichloro-4-pyridyl-amino- | —OH | —H | 2 |
| 24 | 2-trifluoro-methylbenzyl- | 3,5-dichloro-4-pyridyl-amino- | —OH | —H | 2 |
| 25 | 2-fluorobenzyl- | N-methyl-4-pyridyl-amino- | —OH | —H | 2 |
| 26 | 2-fluorobenzyl- | 2,6-dimethyl-4-pyridyl-amino- | —OH | —H | 2 |
| 27 | 2-carboxy-benzyl- | 3,5-dichloro-4-pyridyl-amino- | —OH | —H | 2 |

The compounds according to the invention are powerful inhibitors of phosphodiesterase 4. Their therapeutic potential is verified in vivo by, for example, inhibiting the asthmatic late-phase reaction (eosinophilia), and by inhibiting LPS-induced neutrophilia, in rats.

Example 4

Inhibiting Phosphodiesterase 4

The PDE 4 activity is determined using enzyme preparations from human polymorphonuclear lymphocytes (PMNLs).

Human blood (buffy coats) was anticoagulated with citrate. The platelet-rich plasma in the supernatant is separated from the erythrocytes and leucocytes by centrifuging at 700×g for 20 minutes at room temperature (RT). The PMNLs for the PDE 4 determination are isolated by means of a subsequent dextran sedimentation followed by a gradient centrifugation using Ficoll-Paque. After the cells have been washed twice, the erythrocytes which are still present are lysed within 6 minutes by adding 10 ml of hypotonic buffer (155 mM $NH_4Cl$, 10 mM $NaHCO_3$, 0.1 mM EDTA, pH=7.4) at 4° C. The PMNLs, which are still intact, are washed a further two times with PBS and lysed by ultrasonication. The supernatant obtained after centrifuging at 48 000×g at 4° C. for one hour contains the cytosolic PDE 4 fraction and is used for the PDE 4 measurements.

The phosphodiesterase activity is measured using a modified Amersham Pharmacia Biotech method, i.e. an SPA (scintillation proximity assay) assay. The reaction mixtures contain buffer (50 mM tris-HCl (pH 7.4), 5 mM $MgCl_2$, 100 µM cGMP), varying concentrations of the inhibitors, and the corresponding enzyme preparation. The reaction is started by adding the substrate, i.e. 0.5 µM [$^3$H]-cAMP. The final volume is 100 µl. Test substances are prepared as stock solutions in DMSO. The concentration of DMSO in the reaction mixture is 1% v/v. This DMSO concentration has no effect on PDE activity. After the reaction has been started by adding the substrate, the samples are incubated at 37° C. for 30 minutes. The reaction is stopped by adding a defined quantity of SPA beads and the samples are measured in a beta counter after one hour. The nonspecific enzyme activity (i.e. the blank) is determined in the presence of 100 µM rolipram and subtracted from the test values. The incubation mixtures for the PDE 4 assay contain 100 µM cGMP in order to inhibit any contamination of PDE 3 which may be present.

In regard to inhibiting phosphodiesterase 4, the compounds according to the invention were found to have $IC_{50}$ values in the range from $10^{-9}$ to $10^{-5}$ M. The selectivity towards PDE types 3, 5 and 7 is a factor of from 100 to 10,000.

The PDE 4 inhibition results obtained with selected application examples are compiled in the following table:

| Compound | Inhibition of PDE 4 $IC_{50}$ [µmol/l] |
|---|---|
| 2 | 0.002 |
| 4 | 0.938 |
| 5 | 0.015 |
| 6 | 0.001 |
| 7 | 0.002 |
| 8 | 0.002 |
| 15 | 0.020 |
| 16 | 0.030 |
| 17 | 0.141 |
| 22 | 0.003 |

Example 5

Inhibiting Late-Phase Eosinophilia 48 h After Inhalative Ovalbumin Challenge Formed On Actively Sensitized Brown Norway Rats The inhibition exerted by the substances according to the invention on pulmonary eosinophil infiltration is examined in male Brown Norway rats (200–250 g) which have been actively sensitized against ovalbumin (OVA). The sensitization is effected by subcutaneously injecting a suspension of 10 µg of OVA, together with 20 mg of aluminium hydroxide as adjuvant, in 0.5 ml of physiological sodium chloride solution per animal on days 1, 14 and 21. In addition to this, each of the animals is injected at the same time with 0.25 ml of *Bordetalla pertussis* vaccine dilution i.p. On the 28th day of the experiment, the animals are placed individually in open 1 l Plexiglass boxes which are connected to a head/nose exposure appliance. The animals are exposed to an aerosol consisting of a 1.0% suspension of ovalbumin (Allergen Challenge). The ovalbumin aerosol is generated using a compressed air (0.2 MPa)-driven nebulizer (Bird micro nebulizer, Palm Springs Calif., USA). The exposure time is 1 hour, with normal controls likewise being nebulized for 1 hour with an aerosol consisting of a 0.9% solution of sodium chloride.

48 hours after the allergen challenge, there is a massive immigration of eosinophilic granulocytes into the lungs of the animals. At this time, the animals are anaesthetized with an overdose of ethylurethane (1.5 g/kg of body weight, given i.p.) and a bronchoalveolar lavage (BAL) is carried out using 3×4 ml of Hank's balance solution. The total cell count, and the number of eosinophilic granulocytes, in the pooled BAL liquid are then determined using an automatic haemocytometer (Bayer Diagnostics Technicon H1E). For each animal, the eosinophils (EOS) in the BAL are calculated in $10^6$/animal: EOS/µl×BAL recovery (ml)=EOS/animal. Two control groups (nebulization with physiological sodium chloride solution and nebulization with OVA solution) are included in each test.

The percentage inhibition of the eosinophilia in the substance-treated experimental group is calculated using the following formula:

$$\{((OVAC-SC)-(OVAD-SC))/(OVAC-SC)\} \times 100\% = \% \text{ inhibition}$$

(SC=control group treated with vehicle and challenged with 0.9% sodium chloride solution; OVAC=control group treated with vehicle and challenged with 1% of ovalbumin suspension; OVAD=experimental group treated with substance and challenged with 1% of ovalbumin suspension)

The test substances are administered intraperitoneally or orally, 2 hours prior to the allergen challenge, as a suspension in 10% polyethylene glycol 300 and 0.5% 5-hydroxyethyl cellulose. The control groups are treated with the vehicle in accordance with the manner in which the test substance is administered.

Following intraperitoneal administration of 10 mg/kg the compounds according to the invention inhibit late-phase eosinophilia by from 30% to 100%, while they inhibit it by from 30% to 75% following the oral administration of 30 mg/kg.

The compounds according to the invention are consequently particularly suitable for producing pharmaceuticals for treating diseases which are associated with the activity of eosinophils.

Example 6

Inhibiting Lipopolysaccharide (LPS)-Induced Pulmonary Neutrophilia in Lewis Rats The ability of the substances according to the invention to inhibit pulmonary neutrophil infiltration is examined in male Lewis rats (200–350 g). On the day of the experiment, the animals are placed individually in open 1 l Plexiglass boxes which are connected to a head/nose exposure appliance. The animals are exposed to an aerosol consisting of a suspension of lipopolysaccharide (100 μg of LPS/ml of 0.1% hydroxylamine solution) in PBS (LPS provocation). The LPS/hydroxylamine aerosol is generated using a compressed air (0.2 MPa)-driven nebulizer (Bird micro nebulizer, Palm Springs Calif., USA). The exposure time is 40 minutes, with normal controls likewise being nebulized for 40 minutes with an aerosol consisting of a 0.1% solution of hydroxylamine in PBS.

6 hours after the LPS provocation, there is a maximal and massive immigration of neutrophilic granulocytes into the lungs of the animals. At this time, the animals are anaesthetized with an overdose of ethylurethane (1.5 g/kg of body weight, given i.p.) and a bronchoalveolar lavage (BAL) is carried out using 3×4 ml of Hank's balance solution. The total cell count, and the number of neutrophilic granulocytes, in the pooled BAL liquid are then determined using an automatic haemocytometer (Bayer Diagnostics Technicon H1E). In the case of each animal, the neutrophils (NEUTRO) in the BAL are calculated in $10^6$/animal: NEUTRO/μl×BAL recovery (ml)=NEUTRO/animal.

Two control groups (nebulization with a 0.1% hydroxylamine solution in PBS and nebulization with 100 μg of LPS/ml of 0.1% hydroxylamine solution in PBS) are included in each test. The percentage inhibition of the neutrophilia in the substance-treated experimental group is calculated using the following formula:

$$\{((LPSC-SC)-(LPSD-SC))/(LPSC-SC)\} \times 100\% = \% \text{ inhibition}$$

SC=control group treated with vehicle and challenged with 0.1% hydroxylamine solution; LPSC=control group treated with vehicle and challenged with LPS (100 μg/ml of 0.1% hydroxylamine solution); LPSD=experimental group treated with substance and challenged with LPS (100 μg/ml of 0.1% hydroxylamine solution)

The test substances are administered orally, 2 hours prior to the LPS provocation, as a suspension in 10% polyethylene glycol 300 and 0.5% 5-hydroxyethyl cellulose. The control groups are treated with the vehicle in accordance with the mode of administration used for the test substance.

Following oral administration of 1 mg/kg, the compounds according to the invention inhibit the neutrophilia by from 30% to 90% and are consequently particularly suitable for producing pharmaceuticals for treating diseases which are associated with the activity of neutrophils.

The invention claimed is:

1. A compound of formula 1,

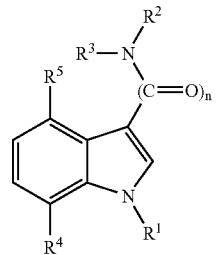

wherein n is 1 or 2, and $R^1$ is —$C_{1-10}$-alkyl, which is straight-chain or branched and substituted, once or more than once, by mono-, bi- or tricyclic saturated or monounsaturated or polyunsaturated carbocycles having 3–14 ring members, where the carbocyclic substituents are substituted once or more than once by —$NO_2$ and can be substituted, once or more than once, by —$C_{1-6}$-alkyl, —OH, —$NH_2$, —$NHC_{1-6}$-alkyl, —$N(C_{1-6}$-alkyl$)_2$, —$NO_2$, —CN, —F, —Cl, —Br, —I, —O—$C_{1-6}$-alkyl, —S—$C_{1-6}$-alkyl, —$SO_3H$, —$SO_2C_{1-6}$-alkyl, —$OSO_2C_{1-6}$alkyl, —COOH, —(CO)$C_{1-5}$-alkyl or —O(CO)$C_{1-5}$-alkyl, and where the alkyl groups on the carbocyclic substituents can be optionally substituted, once or more than once, by —OH, —SH, —$NH_2$, —F, —Cl, —Br, —I, —$SO_3H$ or —COOH;

$R^2$ and $R^3$ (i) are, in each case independently of each other, hydrogen or —$C_{1-5}$-alkyl, which is optionally substituted, once or more than once, by —OH, —SH, —$NH_2$, —$NHC_{1-6}$-alkyl, —$N(C_{1-6}$-alkyl$)_2$, —$NO_2$, —CN, —F, —Cl, —Br, —I, —O—$C_{1-6}$-alkyl, —S—$C_{1-6}$-alkyl, -phenyl or -pyridyl, -phenyl, which is optionally substituted, once or more than once, by —$C_{1-3}$-alkyl, —OH, —SH, —$NH_2$, —$NHC_{1-3}$-alkyl, —$N(C_{1-3}$-alkyl$)_2$, —$NO_2$, —CN, —COOH, —$COOC_{1-3}$-alkyl, —F —Cl, —Br, —I, —O—$C_{1-3}$-alkyl, —S—$C_{1-3}$-alkyl or —O(CO)—$C_{1-3}$-alkyl, -pyridyl, which is optionally substituted, once or more than once, by —$C_{1-3}$-alkyl, —OH, —SH, —$NO_2$, —CN, —COOH, —$COOC_{1-3}$-alkyl, —F, —Cl, —Br, —I, —O—$C_{1-3}$-alkyl, —S—$C_{1-3}$-alkyl or —O(CO)—$C_{1-3}$-alkyl, where only one of $R^2$ and $R^3$ is hydrogen and where the alkyl groups on the carbocyclic and heterocyclic substituents can, for their part, be optionally substituted, once or more than once, by —OH, —SH, —$NH_2$, —F, —Cl, —Br, —I, —$SO_3H$, —COOH, —(CO)—$C_{1-5}$-alkyl, or —O(CO)$C_{1-5}$-alkyl, or (ii) $NR^2R^3$ together form a saturated or unsaturated five-membered or six-membered ring which can contain up to 3 heteroatoms, preferably N, S and O, and which is optionally substituted, once or more than once, by —$C_{1-3}$-alkyl, —OH, —SH, —$NO_2$, —CN, —COOH, —$COOC_{1-3}$-alkyl, —F, —Cl —Br, —I, —O—$C_{1-3}$-alkyl, —S—$C_{1-3}$-alkyl or —O(CO)—$C_{1-3}$-alkyl, R⁴ and R⁵ are —H or —OH, where at least one of the two must be —OH, or salts of the compounds according to formula 1.

2. A compound according to claim 1, wherein said compound has an asymmetric carbon atom in the D form or L form, or D,L mixtures or, when more than one asymmetrical carbon atom is present, the diastereomeric forms.

3. A compound according to claim 1, wherein n is 2.

4. A compound according to claim 1, wherein $R^4$=—OH and $R^5$=—H.

5. A compound according to claim 1, wherein —$NR^2R^3$ is a phenylamino or pyridylamino which is substituted by one or more halogen atoms.

6. A compound according to claim 1, wherein $R^1$ is a substituted benzyl radical.

7. A compound according to claim 6, wherein the benzyl radical contains at least one substituent in the ortho position on the phenyl ring.

8. A compound according to claim 1, selected from the group consisting of,
N-(3,5-dichloropyridin-4-yl)-[1-(3-nitrobenzyl)-7-hydroxyindol-3yl]glyoxylic acid amide
and physiologically tolerated salts thereof.

9. A process for preparing a compound according to claim 1, comprising reacting an indole-3-carboxylic acid of formula 2:

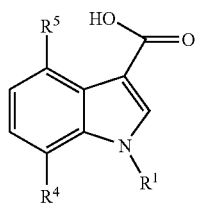

formula 2 with an acid chloride to form the analogous indole-3-carbonyl chloride of the formula 3

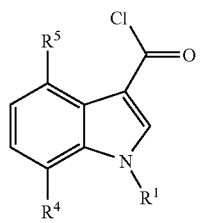

formula 3 reacting the compound of formula 3 with a primary and a secondary amine to form the corresponding amide and eliminating a protecting group to form a compound of formula 1, wherein n=1.

10. A process according to claim 9, wherein said acid chloride is thionyl chloride or oxalyl chloride to synthesize the indole-3-carbonyl chlorides according to formula 3.

11. A process according to claim 9, wherein said indole-3-carbonyl chloride according to formula 3 are reacted with primary or secondary amines in the presence of an auxiliary base.

12. A process according to claim 9, wherein said indole-3-carbonyla chloride is reacted with a primar or secondary amine in the presence of an excess of amine.

13. A process according to claim 12, wherein the excess amine is a tertiary amine.

14. A process according to claim 11, wherein indole-3-carbonyl chloride is reacted in the presence of an inorganic base.

15. A process for preparing a compound according to claim 1, comprising reacting an indole formula 4

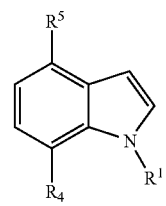

formula 4 with oxalyl chloride to form the analogous indol-3-ylglyoxylyl chloride of formula 5

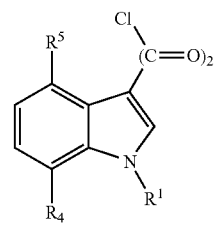

formula 5 reacting the compound of formula 5 with a primary or secondary amine to form the corresponding amide and eliminating a protecting group to form a compound according to formula 1, wherein n is 2.

16. A process according to claim 15, wherein indol-3-ylglyoxylyl chlorides according to formula 5 are reacted with primary or secondary amines in the presence of an auxiliary base.

* * * * *